(12) United States Patent
Faynberg et al.

(10) Patent No.: US 11,553,398 B2
(45) Date of Patent: Jan. 10, 2023

(54) SYSTEMS AND METHODS FOR INTERNET OF THINGS SECURITY ENVIRONMENT

(71) Applicant: CABLE TELEVISION LABORATORIES, INC, Louisville, CO (US)

(72) Inventors: Igor Faynberg, East Brunswick, NJ (US); Darshak Thakore, Broomfield, CO (US); Donald E. A. Clarke, Louisville, CO (US); Steven J. Goeringer, Westminster, CO (US)

(73) Assignee: Cable Television Laboratories, Inc., Louisville, CO (US)

( * ) Notice: Subject to any disclaimer, the term of this patent is extended or adjusted under 35 U.S.C. 154(b) by 445 days.

(21) Appl. No.: 16/353,558

(22) Filed: Mar. 14, 2019

(65) Prior Publication Data
US 2019/0215755 A1 Jul. 11, 2019

Related U.S. Application Data

(63) Continuation-in-part of application No. 16/176,865, filed on Oct. 31, 2018.
(Continued)

(51) Int. Cl.
*H04W 40/20* (2009.01)
*H04L 9/40* (2022.01)
(Continued)

(52) U.S. Cl.
CPC ......... *H04W 40/20* (2013.01); *H04L 63/0428* (2013.01); *H04L 63/1416* (2013.01);
(Continued)

(58) Field of Classification Search
CPC ... H04W 40/20; H04W 12/37; H04W 12/121; H04W 4/70; H04W 64/00;
(Continued)

(56) References Cited

U.S. PATENT DOCUMENTS 8,718,797 B1 * 5/2014 Addepalli ............. H04W 40/02
700/83
9,874,923 B1 * 1/2018 Brown ...................... G06F 1/26
(Continued)

*Primary Examiner* — Cheng-Feng Huang
(74) *Attorney, Agent, or Firm* — Armstrong Teasdale LLP

(57) ABSTRACT

A system for monitoring the communication with a connected Internet of Things (IoT) device is provided. The system includes a first computing device including a least one processor in communication with at least one memory device. The at least one memory device stores a plurality of instructions, which when executed by the at least one processor cause the at least one processor to execute an IoT device communication application. The IoT device communication application monitors the IoT device. The instructions also cause the at least one processor to store IoT device data including a current location of the IoT device, determine an optimal communication path between the IoT device communication application and the IoT device based on the IoT device data, and transfer execution of the IoT device communication application to a second computing device based on the optimal communication path.

18 Claims, 5 Drawing Sheets

Related U.S. Application Data

(60) Provisional application No. 62/642,923, filed on Mar. 14, 2018, provisional application No. 62/579,592, filed on Oct. 31, 2017.

(51) Int. Cl.
| | |
|---|---|
| *H04W 64/00* | (2009.01) |
| *H04L 67/10* | (2022.01) |
| *H04W 4/70* | (2018.01) |
| *H04W 12/37* | (2021.01) |
| *H04W 12/121* | (2021.01) |
| *H04L 67/12* | (2022.01) |

(52) U.S. Cl.
CPC .............. *H04L 63/20* (2013.01); *H04L 67/10* (2013.01); *H04W 4/70* (2018.02); *H04W 12/121* (2021.01); *H04W 12/37* (2021.01); *H04W 64/00* (2013.01); *H04L 63/145* (2013.01); *H04L 63/1458* (2013.01); *H04L 67/12* (2013.01)

(58) Field of Classification Search
CPC . H04L 63/1416; H04L 67/10; H04L 63/0428; H04L 63/20; H04L 63/145; H04L 63/1458; H04L 67/12; G16H 10/00
See application file for complete search history.

(56) References Cited

U.S. PATENT DOCUMENTS

| | | | |
|---|---|---|---|
| 10,021,765 B1* | 7/2018 | Elliot | H04L 67/025 |
| 2014/0098685 A1* | 4/2014 | Shattil | H04L 41/147 |
| | | | 370/252 |
| 2015/0188935 A1* | 7/2015 | Vasseur | G06N 20/00 |
| | | | 726/23 |
| 2016/0066137 A1* | 3/2016 | Kulkarni | G01S 5/0221 |
| | | | 455/456.1 |
| 2016/0085977 A1* | 3/2016 | Oh | G06F 21/51 |
| | | | 726/20 |
| 2017/0257129 A1* | 9/2017 | Egner | H04B 1/385 |
| 2017/0353556 A1* | 12/2017 | Seenappa | H04L 67/12 |
| 2018/0109308 A1* | 4/2018 | Leroux | H04B 7/2606 |
| 2018/0288179 A1* | 10/2018 | Bhatia | H04L 67/28 |
| 2019/0045412 A1* | 2/2019 | Shivam | H04W 40/02 |

* cited by examiner ered security of their devices. This problem is expanding as the task of ensuring the security of a single telephone or personal computer is constantly growing, let alone ensuring the security of all of an individual's IoT devices. The absence of a single root-of-trust Public Key Infrastructure (PKI) renders the task of ensuring the security of a typical mobile phone extraordinarily difficult, given the proliferation of a multitude of obscure root-key certificates.

SYSTEMS AND METHODS FOR INTERNET OF THINGS SECURITY ENVIRONMENT

CROSS REFERENCE TO RELATED APPLICATIONS

This application is a continuation-in-part of U.S. patent application Ser. No. 16/176,865, filed Oct. 31, 2018, entitled "SYSTEMS AND METHODS FOR INTERNET OF THINGS SECURITY ENVIRONMENT," which claims the benefit of and priority to U.S. Provisional Patent Application No. 62/579,592, filed Oct. 31, 2017, entitled "METHOD AND APPARATUS FOR ENSURING SECURITY OF THE PRINCIPALS IN THE INTERNET OF THINGS (IOT) ENVIRONMENT," and this application also claims the benefit of and priority to U.S. Provisional Patent Application No. 62/642,923, filed Mar. 14, 2018, entitled "A METHOD AND APPARATUS FOR SUPPORTING SERVICE MOBILITY IN THE INTERNET OF THINGS (IOT) ENVIRONMENT," the entire contents and disclosure of which are incorporated by reference in its entirety.

BACKGROUND

The field of the disclosure relates generally to the security of Internet of Things (IoT) devices, and more particularly, to systems and methods for protecting data and communications provided to and by IoT devices.

The emerging IoT environment includes end-user devices (i.e., the "things" in the IoT) ranging from sensors to home utilities to medical devices. This environment not only inherits all the known and troublesome security problems present in the Internet, but also augments these problems in additional manners. One such problem is that the human users of these devices are not consistent in enforcing the security of their devices. This problem is expanding as the task of ensuring the security of a single telephone or personal computer is constantly growing, let alone ensuring the security of all of an individual's IoT devices. The absence of a single root-of-trust Public Key Infrastructure (PKI) renders the task of ensuring the security of a typical mobile phone extraordinarily difficult, given the proliferation of a multitude of obscure root-key certificates.

In addition, other factors that make the maintenance of the security of IoT devices very hard, if not outright impossible, for most human users is the necessity to maintain (securely) and remember various passwords, including the password for accessing the device, properly administering software updates, and otherwise having specialized device security knowledge that requires years of specialized development and training. Furthermore, in some cases, the individual IoT devices may have malicious code pre-installed on the device.

The consequences of a security failure to the end users can easily be a matter of life or death (as in cases of implanted medical devices or vehicles), not to mention loss of privacy or financial losses because of identity theft. The owners of the things/devices are not the only ones who will suffer such consequences. When the access to a device is stolen, just as it happens today with personal computers, the device itself becomes a vector for spreading viruses and conducting denial of service attacks that potentially can have catastrophic effect on other principals, including, but not limited to the service providers who offer the IoT services and the network operators who host such service providers.

SUMMARY

In an embodiment, a system for monitoring the security of a connected Internet of Things (IoT) device includes a network doppelganger (ND) computer device. The ND computer device includes at least one processor in communication with at least one memory device. The ND computer device is in communication with the IoT device and a service provider computer device associated with the IoT device. The at least one memory device stores a plurality of instructions, which when executed by the at least one processor cause the at least one processor to store a plurality of policies associated with the service provider computer device, receive a communication from the IoT device addressed to the service provider computer device, analyze the communication in view of the plurality of policies to determine whether the communication is approved, and if the communication is approved, route the communication to the service provider computer device.

In another embodiment, a system for monitoring the communication with a connected Internet of Things (IoT) device is provided. The system includes a first computing device comprising a least one processor in communication with at least one memory device. The first computing device is in communication with the IoT device. The at least one memory device stores a plurality of instructions, which when executed by the at least one processor cause the at least one processor to execute an IoT device communication application. The IoT device communication application monitors the IoT device. The instructions also cause the at least one processor to store, in the at least one memory device, IoT device data including a current location of the IoT device. The instructions further cause the at least one processor to determine an optimal communication path between the IoT device communication application and the IoT device based on the IoT device data. In addition, the instructions also cause the at least one processor to transfer execution of the IoT device communication application to a second computing device based on the optimal communication path.

BRIEF DESCRIPTION OF THE DRAWINGS

These and other features, aspects, and advantages of the present disclosure will become better understood when the following detailed description is read with reference to the following accompanying drawings, in which like characters represent like parts throughout the drawings.

Figure 1:
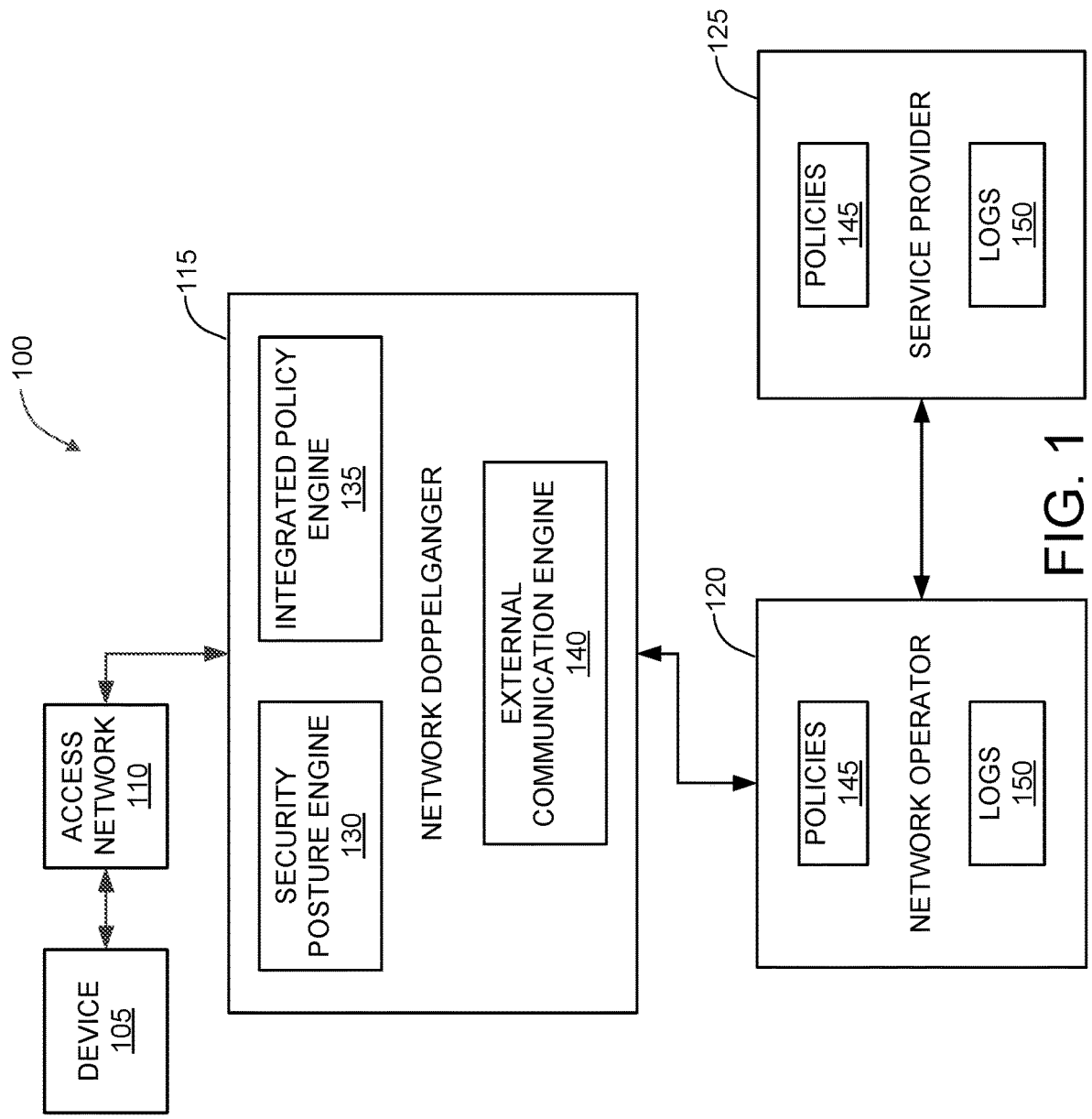
FIG. 1 is a schematic illustration of an IoT device network security system that utilizes a network doppelganger to securely monitor and maintain the security status of the IoT device, according to an embodiment.

Unless otherwise indicated, the drawings provided herein are meant to illustrate features of embodiments of this disclosure. These features are believed to be applicable in a wide variety of systems including one or more embodiments of this disclosure. As such, the drawings are not meant to include all conventional features known by those of ordinary skill in the art to be required for the practice of the embodiments disclosed herein.

DETAILED DESCRIPTION

In the following specification and the claims, reference will be made to a number of terms, which shall be defined to have the following meanings.

The singular forms "a," "an," and "the" include plural references unless the context clearly dictates otherwise.

"Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the terms "processor" and "computer" and related terms, e.g., "processing device", "computing device", and "controller" are not limited to just those integrated circuits referred to in the art as a computer, but broadly refers to a microcontroller, a microcomputer, a programmable logic controller (PLC), an application specific integrated circuit (ASIC), and other programmable circuits, and these terms are used interchangeably herein. In the embodiments described herein, memory may include, but is not limited to, a computer-readable medium, such as a random access memory (RAM), and a computer-readable non-volatile medium, such as flash memory. Alternatively, a floppy disk, a compact disc-read only memory (CD-ROM), a magneto-optical disk (MOD), and/or a digital versatile disc (DVD) may also be used. Also, in the embodiments described herein, additional input channels may be, but are not limited to, computer peripherals associated with an operator interface such as a mouse and a keyboard. Alternatively, other computer peripherals may also be used that may include, for example, but not be limited to, a scanner. Furthermore, in the exemplary embodiment, additional output channels may include, but not be limited to, an operator interface monitor.

Further, as used herein, the terms "software" and "firmware" are interchangeable, and include any computer program storage in memory for execution by personal computers, workstations, clients, and servers.

As used herein, the term "non-transitory computer-readable media" is intended to be representative of any tangible computer-based device implemented in any method or technology for short-term and long-term storage of information, such as, computer-readable instructions, data structures, program modules and sub-modules, or other data in any device. Therefore, the methods described herein may be encoded as executable instructions embodied in a tangible, non-transitory, computer readable medium, including, without limitation, a storage device and a memory device. Such instructions, when executed by a processor, cause the processor to perform at least a portion of the methods described herein. Moreover, as used herein, the term "non-transitory computer-readable media" includes all tangible, computer-readable media, including, without limitation, non-transitory computer storage devices, including, without limitation, volatile and nonvolatile media, and removable and non-removable media such as a firmware, physical and virtual storage, CD-ROMs, DVDs, and any other digital source such as a network or the Internet, as well as yet to be developed digital means, with the sole exception being a transitory, propagating signal.

The embodiments described herein provide systems and methods for monitoring and maintaining the security status of a connected IoT device. In an exemplary embodiment, a network doppelganger interfaces between a device, such as an IoT device and a service provider that is in communication with the device. The network doppelganger acts as a protective interface, or "midbox", that monitors communications between the device and the service provider. In some embodiments, the network doppelganger monitors for malicious activities on the part of the device and protects other devices on the network and the service provider from such activities.

In some further embodiments, the network doppelganger acts to protect the device by ensure that proper security procedures are followed. These security procedures may be defined by one or more of the service provider, the network that the service provider is running on, and/or the network that the device is connected to. These security procedures could include, ensuring the device follows proper password security, ensuring the device is up to date with software patches, and monitoring and potentially communications from and to the device for potential security issues and/or events. Furthermore, in some embodiments, the network doppelganger is connected to and monitors multiple devices simultaneously.

In some embodiments, the network doppelganger acts as an effective point of top insertion for law enforcement activities to lawfully intercept communications, such as those under the Communications Assistance for Law Enforcement Act (CALEA).

In some embodiments, the device is mobile. In these embodiments, the access network function may be provided by a different network operator, such that every time that the device changes network, the network doppelganger acts to protect that network and integrate the policies of the connected to network.

In some embodiments, a service stack is associated with each device on the server. In these embodiments, the system moves the service stack between servers based on the location of the mobile device, the quality of service (QoS) between the mobile device and the server, and the computational loads of the various servers.

FIG. 1 is a schematic illustration of a network security system 100 that utilizes a network doppelganger 115 to securely monitor and maintain the security status of a device 105, according to an embodiment.

The device 105, may include, but is not limited to an IoT device, a client computing device (e.g., a smartphone, tablet, laptop, desktop computing device, wearable, or other computing device), or another type of device that allows the system to work as described herein. In some embodiments, the device 105 may be a medical device that is either remotely monitored and/or controlled.

In an exemplary embodiment, the device 105 connects to a network operator 120, such as through an access network 110. The access network 110 may be, but is not limited to, a home or enterprise network. In some embodiments, the device 105 is mobile. In these embodiments, the access network function may be provided by a different network operator. Through the network operator 120, the device 105 is connected to one or more service providers 125. Service providers 125 are services that provide functionality to the device 105. In some further embodiments, the service provider 125 is a network provider or is hosted by the network provider. In the exemplary embodiment, both the network operator 120 and the service provider 125 include policies 145 and store logs 150.

In some embodiments, the service providers 125 act as data collection and storage for the device 105, which may be a sensor. In other embodiments, the service providers 125 receive data from the device 105 and provide instructions to the device 105. In some embodiments, the device 105 is a medical device and the service provider 125 is associated with a medical office. For all practical purposes, access to the service providers 125 is represented by a data communication interface, such as, but not limited to, a Remote Procedure Call (RPC) or a Hyper-Text Transfer Protocol-based application programmer's interface (API).

In the exemplary embodiment, data and communication between the device 105 and the service provider 125 is routed through the network doppelganger 115. The network doppelganger 115 acts as a midbox. In the exemplary embodiment, the network doppelganger 115 is configured to constantly evaluate the security properties of the device 105. The network doppelganger 115 is also configured to proactively take measures to enforce the security of the device 105. The network doppelganger 115 is further configured to protect the network operator 120 and the service provider 125 from malicious activity directed from the device 105.

In the exemplary embodiment, the network doppelganger 115 includes a security posture engine 130, an integrated policy engine 135, and an external communication engine 140. In the embodiment depicted in FIG. 1, the network doppelganger 115 is illustrated as a midbox between the access network 110, the network operator 120, and the service provider 125. In practical implementation, the network doppelganger 115 may be an integrated hardware or software component of the access network 110, the network operator 120, or the service provider 125, or may be a separate entity in communication with these other system elements. In some embodiments, the network doppelganger 115 is virtualized, and may optionally distribute individual functions among one or more of the several system components. In at least one embodiment, the service provider 125 is the network operator 120 itself, or simply hosted by the network provider 120.

In the exemplary embodiment, the security posture engine 130 is configured to poll the device 105 to determine the validity and strength of any password associated with the device 105. The security posture engine 130 is also configured to force the end user of the device 105 to change the password to a more secure password when essential. For example, the security posture engine 130 may transmit messages instructing the end user to change the password of the device 105. These instructions may also include guidelines for a strong password. In some embodiments, the security posture engine 130 transmits the instructions directly to the device 105 to be displayed by the device 105 to the end user. In other embodiments, the security posture engine 130 transmits the instructions to the service provider 125. The service provider 125 then contacts the end user and instructs the end user to change the device's password.

In the exemplary embodiment, the security posture engine 130 is also configured to check the integrity of the hardware and the software of the device 105. In some embodiments, the integrity check is performed by an integrity verification, such as attestation. In some of these embodiments, the security posture engine 130 transmits an integrity check which includes a nonce to the device 105. The device 105 generates a signature using the nonce and information about the device itself. The device 105 responds to the integrity check with the generated signature. The security posture engine 130 then analyzes the generated signature to determine a trust level for the device 105.

In the exemplary embodiment, the security posture engine 130 analyzes the software and hardware of the device 105 and determines if software patches or other updates are required to the device 105. If a patch or update is required, then the security posture engine 130 instructs the device 105 to install the patch or update. In some embodiments, the security posture engine 130 transmits the patch and/or update to the device 105 for the device 105 to install. In other embodiments, the security posture engine 130 takes control of the device 105 and installs the patch or update remotely.

In the exemplary embodiment, the security posture engine 130 also logs essential security events. The security posture engine 130 transmits the logs 150 to either the network operator 120 or the service provider 125 as necessary. In the exemplary embodiment, the security events are based on the policies 145 of the network operator 120 and/or the service provider 125. The policies 145 are received from the network operator 120 and/or the service provider 125 by the integrated policy engine 135, which then communicates the policies 145 to the security posture engine 130 to know which events to log. Within this description, the term "security event" is used somewhat broadly, and may be defined by the policies 145. For example, in the case of a medical device, having the device be turned off or appear to be inoperable may be an event that needs to be logged. In some cases, the events may also cause alarms to be triggered. In these cases, the network doppelganger 115 transmits an alarm to at least one of the network operator 120, the service provider 125, and the device 105.

In the exemplary embodiment, the external communication engine 140 monitors the communications between the device 105 and the rest of the Internet. In some embodiments, the external communication engine 140 modifies these communications to adhere to the network operator 120 and service provider 125 policies 145.

In some embodiments, the external communication engine 140 and the security posture engine 130 use pattern recognition and other machine-learning technologies to detect anomalies. Examples of anomalies include, but are not limited to the presence of viruses, communication patterns that might constitute denial of service attacks, and communications that may be related to Trojans or other remote access of the device 105. The external communication engine 140 and the security posture engine 130 may be connected to respective security monitoring modules.

In some embodiments, the network doppelganger 115 is implemented on standalone hardware as a set of independent processes. In these embodiments, one or more processes may be associated with each of the entities, (i.e., security posture engine 130, the integrated policy engine 135, and the external communication engine 140). In some embodiments, each of the processes is under the control of an operating system. Furthermore, the network doppelganger 115 may be connected to several, separate devices 105 and may be configured to monitor and update each of the connected devices 105. This allows the network doppelganger 115 to be virtualized so that the individual entities can be executed as a container or so that the individual entities can be virtualized as a network appliance. This virtualization feature allows for supporting the mobility of the network doppelganger 115 so that the network doppelganger 115 may support mobile devices 105. In at least one embodiment, a single instance of network doppelganger 115 may be configured to act on behalf of several identical "things," e.g., devices 115.

In some embodiments, a Network Function Virtualization (NFV) environment supports the movement of the above described virtual functions within a network operator's cloud. The NFV environment allows the network doppelganger 115 to support the service agreement (and policies 145) of another network operator's cloud. This allows for the roaming of the device 105, so that the network doppelganger 115 shadows the device 105 to reduce latency and optimize performance of the device 105.

Figure 2:
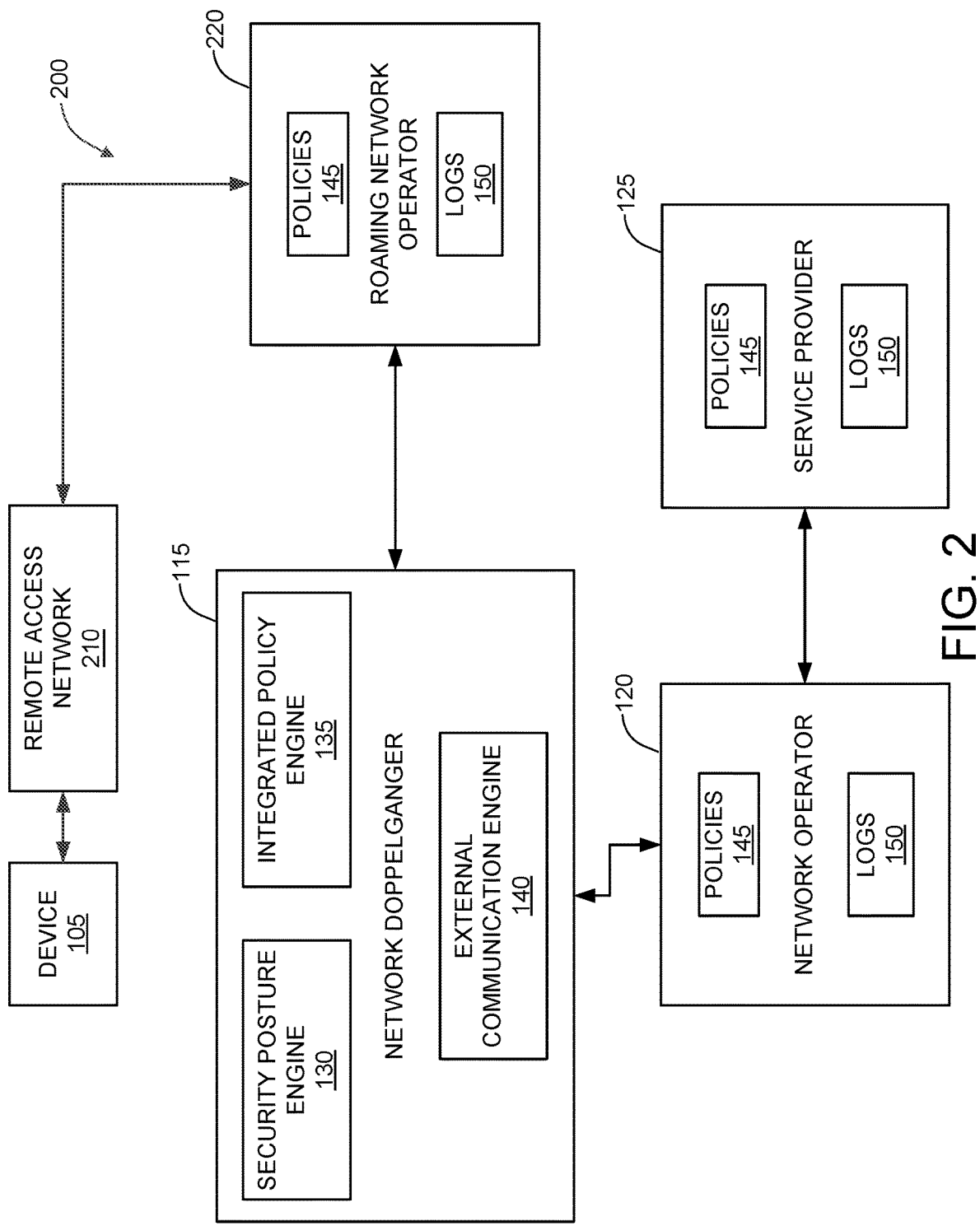
FIG. 2 is a schematic illustration of a roaming network security system that utilizes the network doppelganger shown in FIG. 1 to securely monitor and maintain the security status of a roaming device, according to an embodiment.

FIG. 2 is a schematic illustration of a roaming network security system 200 that utilizes the network doppelganger 115 shown in FIG. 1 to securely monitor and maintain the security status of a roaming device 105, according to an embodiment.

In the roaming system 200, the device 105 attempts to access the network operator 120 and the service provider 125 via a remote access network 210. The remote access network 210 may be any network that allows the device 105 to access the Internet. For example, the remote access network 210 may be, but is not limited to, a cellular network, a network provided by a public location, a place of business, and a vehicle, and a network at another residence. The remote access network 210 is generally associated with a roaming network operator 220, which may be a network provider. The roaming network operator 220 then connects the device with the network doppelganger 115 associated with the device 105. In some embodiments, the roaming network operator 220 contacts the network operator 120, which then instructs the roaming network operator 220 where to locate the network doppelganger 115. In some further embodiments, the roaming network operator 220 includes policies 145 that are communicated to the integrated policy engine 135 of the network doppelganger 115. The security posture engine 130 then uses the policies 145 of the roaming network operator 220 in the operation of the network doppelganger 115. When the device 105 disconnects from the first remote access network 210 and connects to a second remote access network 210, the network doppelganger 115 may receive different policies 145 associated with a different roaming network operator 220.

Figure 3:
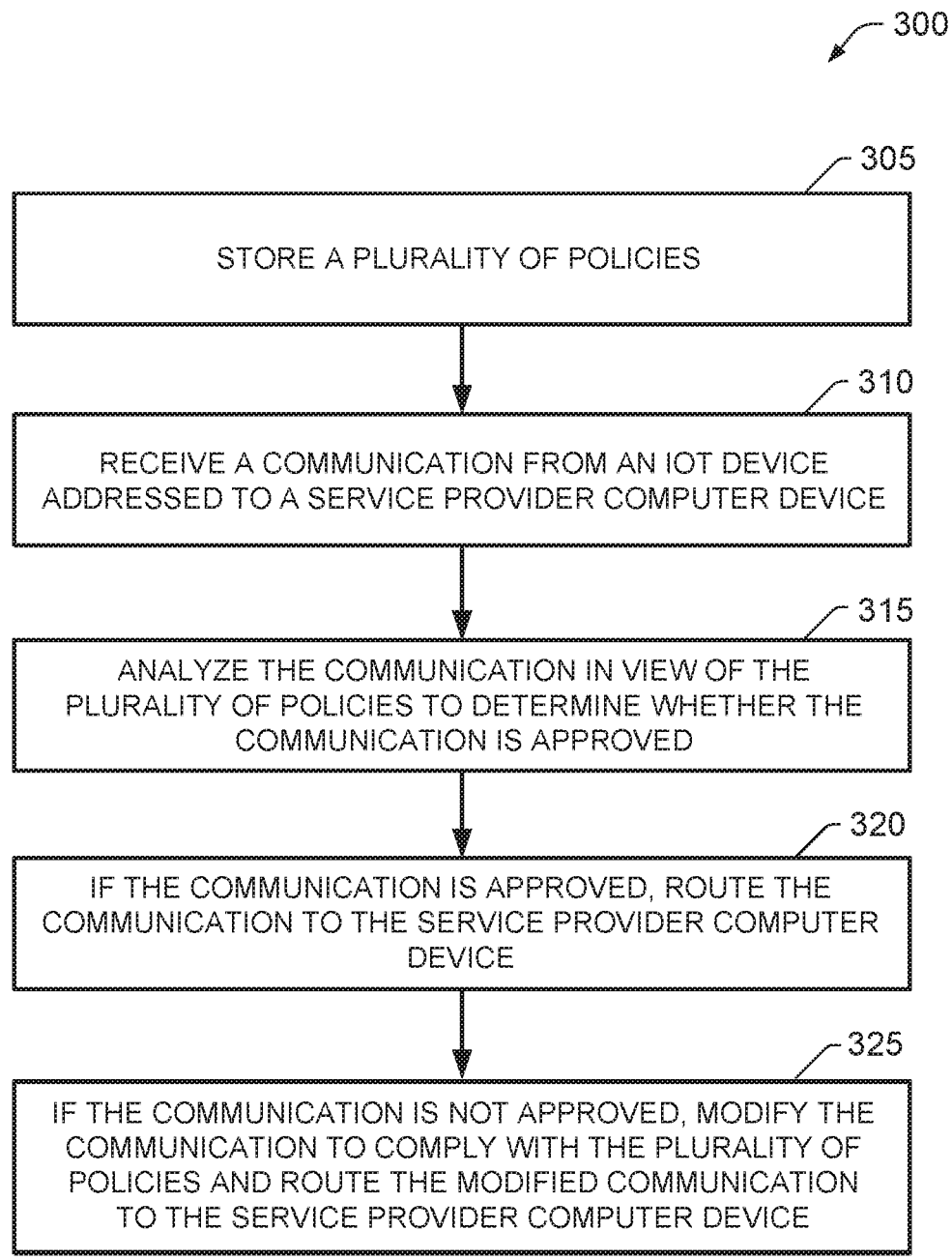
FIG. 3 is a process for securely monitoring and maintaining a security status of a device using the network doppelganger shown in FIG. 1.

FIG. 3 is a process 300 for securely monitoring and maintaining a security status of a device 105 using the network doppelganger 115, both shown in FIG. 1. In the exemplary embodiment, the network doppelganger 115 is executed on a network doppelganger computer device. In other embodiments, the functionality of the network doppelganger 115 is distributed over a plurality of computer devices.

In the exemplary embodiments, the network doppelganger computer device includes at least one processor in communication with at least one memory device. The memory device stores instructions, such that, when executed by the at least one processor, the instructions cause the at least one processor to at least perform the steps of process 300 as described herein.

In the exemplary embodiment, the network doppelganger computer device stores 305 a plurality of policies, such as policies 145. These policies may be associated with the service provider 125 or the network operator 120, both shown in FIG. 1. These policies define actions and restrictions that the associated system applies to devices 105. In the exemplary embodiment, the policies 145 are maintained by the integrated policy engine 135, shown in FIG. 1.

In the exemplary embodiment, the network doppelganger computer device receives 310 a communication from the device 105 addressed to a computer device associated with the service provider 125, hereinafter called the service provider computer device. The communication may include a message, a data packet, streaming data, a request for instructions, and/or any other communication addressed to the service provider 125. In other embodiments, the communication may be directed to the network operator 120 or another device 105. The network doppelganger computer device receives the communication via the access network 110, shown in FIG. 1. The external communication engine 140, shown in FIG. 1, receives the communication.

The network doppelganger computer device analyzes 315 the communication in view of the plurality of policies to determine whether the communication is approved. In the exemplary embodiment, the security posture engine 130, shown in FIG. 1, analyzes 315 the communication to determine if the communication is approved.

If the communication is approved, the network doppelganger computer device routes 320 the communication to the service provider computer device. In some embodiments, the network doppelganger computer device routes 320 the communication to the service provider computer device via one or more computer devices associated with the network operator 120.

If the communication is not approved, the network doppelganger computer device modifies 325 the communication to comply with the plurality of policies and route the modified communication to the service provider computer device. For example the network doppelganger computer device may determine that the communication is too long and split the communication into multiple messages. In some embodiments, the network doppelganger computer device discards the communication if the communication is not approved.

In the exemplary embodiment, communication between the device 105 and the service provider 125 is bi-directional. The network doppelganger computer device receives a second communication from the service provider computer device addressed to the device 105. The network doppelganger computer device analyzes the second communication in view of the plurality of policies associated with the service provider 125 and the network operator 120. If the second communication is approved, the network doppelganger computer device routes the communication to the service provider computer device. If the second communication is not approved, the network doppelganger computer device modifies the communication to comply with the plurality of policies associated with the service provider 125 and the network operator 120 and routes the modified second communication to the device 105.

In some embodiments, the network doppelganger computer device receives password information from the device 105. The network doppelganger computer device analyzes the password information to determine a security level of the password information. The security level may be based on the policies of the network operator 120 and the service provider 125. If the security level of the password information is below a required security threshold, the network doppelganger computer device instructs a user associated with the device 105 to update the password information. In some embodiments, the network doppelganger computer device also transmits guidelines for password security to the user. In these embodiments, the guidelines for password security are based on the plurality of policies. In some further embodiments, the network doppelganger computer device transmits the instruction to the user to at least one of the device 105 and the service provider computer device.

In some embodiments, the network doppelganger computer device requests and receives security information from the device 105. This security information may include, but is not limited to, software and hardware version information. The network doppelganger computer device analyzes the security information based, at least in part, on the plurality of policies. The network doppelganger computer device may then determine that a software update is necessary for the device 105 based on the analysis of the security information. In some embodiments, the network doppelganger computer device transmits an instruction to the device 105 to install the software update. In further embodiments, the network doppelganger computer device transmits the software update to the device 105. In still further embodiments, the network doppelganger computer device remotely controls the device 105 to install the software update.

In some embodiments, the network doppelganger computer device is configured to communicate with a tap computer device. In these embodiments, the network doppelganger computer device transmits communications received from and transmitted to the device 105 to the tap computer device.

Service Mobility Support in the IoT Environment

Figure 4:
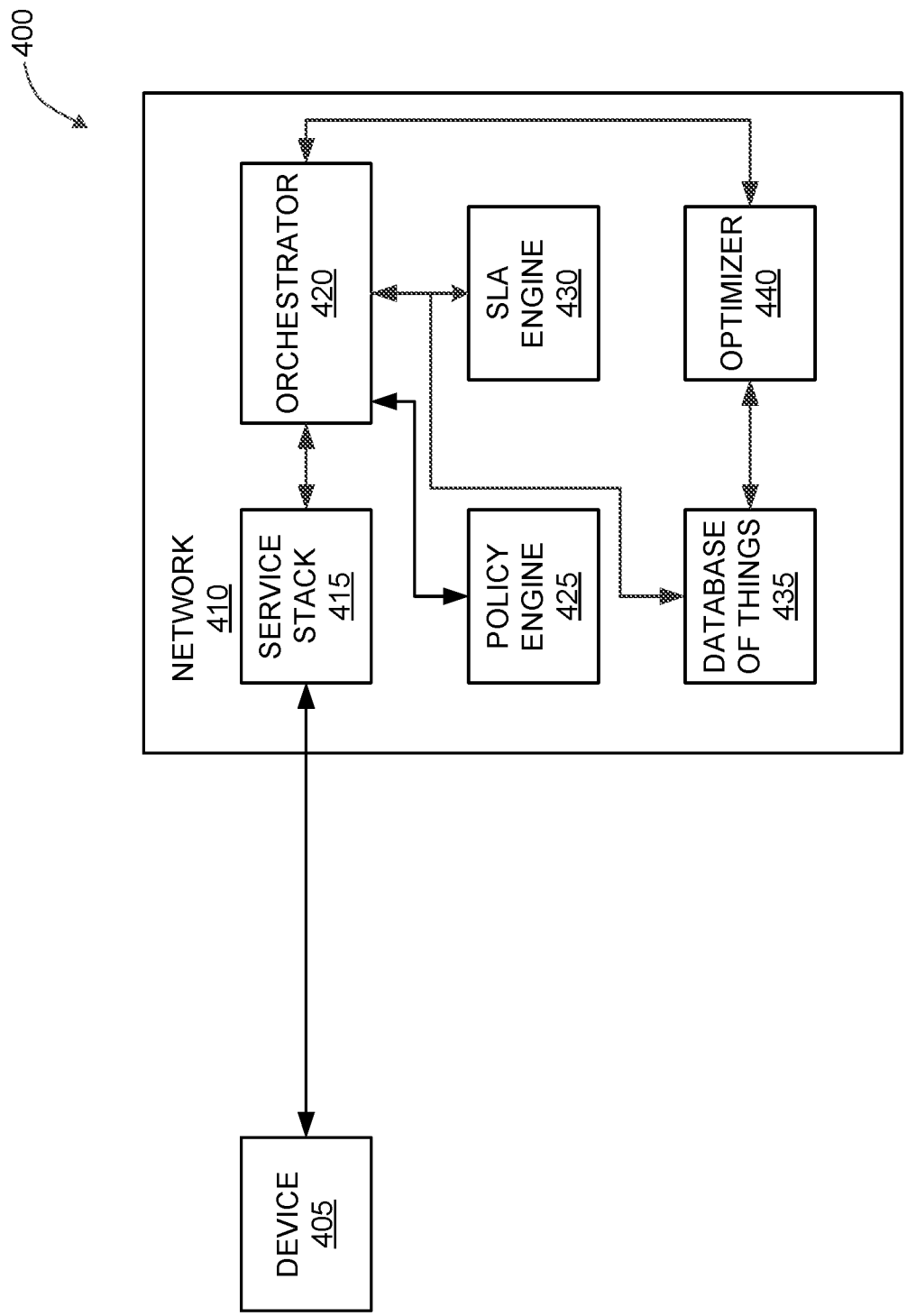
FIG. 4 is a schematic illustration of an IoT device network security system that monitors the location of a roaming device, according to an embodiment.

FIG. 4 is a schematic illustration of an IoT device network security system 400 that utilizes a service stack 415 to monitor the location of a roaming device 405, according to an embodiment.

In system 400, a device 405 connects to a network 410 via a service stack 415. In some embodiments, device 405 is similar to device 105 and network 410 is similar to network operator 120 (both shown in FIG. 1). In some embodiments, network 410 includes one or more data centers. In the some embodiments, the service stack 415 is similar to a virtual network function (VNF) in the network functions virtualization (NFV). The service stack 415 helps to optimize the network services provided to the device 405. In further embodiments, the service stack 415 is a set of virtual machines. In still further embodiments, the service stack 415 is a set of processes isolated in a container. In some embodiments, the service stack 415 is an IoT device communication application, that may be executed on a plurality of computer devices. In some embodiments, network doppelganger 115 (shown in FIG. 1) interfaces between device 405 and network 410 as described above. In the exemplary embodiment, the running machine image, or alternatively, process image) can be copied and transferred among data centers in various networks, including a home network of the user of the device 405.

In the exemplary embodiment, the network 410 includes an orchestrator 420, which creates, monitors, and moves around the VNFs or service stacks 415. In some embodiments, the actions of the orchestrator 420 are dependent on engines that implement the network operator's policies and service level specifications in support of the service level agreement (SLA). In some embodiments, the policies and the SLA may be executed by a policy engine 425 and an SLA engine 430 respectively. Policy engine 425 may be similar to integrated policy engine 135 (shown in FIG. 1).

In the exemplary embodiment, at least one of the network 410 and the network doppelganger 115 tracks the location of the device 405 to determine the optimal location of the service stack 415 in relation to the device 405 that it serves. To support this functionality, the system 400 includes an optimizer 440. In some embodiments, the optimizer 440 is a part of the orchestrator 420 in other embodiments, the optimizer 440 is a part of the network doppelganger 115.

The optimizer 440 works in concert with a database of devices 435 (also known as a database of things) to track and coordinate the devices 405 that are interconnected at various locations and are associated with various networks 410. In the exemplary embodiment, the database of devices 435 stores the current location of each device 405, statistical information associated with the quality of service (QoS), bandwidth used by the device 405 (currently and average over a defined time period), lists of other networks 410 as well as associated costs, and statistics related to the computational power being used (i.e., the current use, average use overtime, peak usage times and locations, etc.) As the location of the device 405, this location information is updated in the database of devices 435. The above list of information stored is not exhaustive and the database of devices 435 may store more or less information to allow the system 400 to work as described herein. In some embodiments, the database of devices 435 is distributed among a multitude of data centers and is kept up-to-date via periodic exchanges of updates among the different parts of the database. In other embodiments, the database of devices 435 is stored in a central repository and copies are provided to various data centers. In some embodiments, the database of devices 435 is globally updated. In other embodiments, local version of the database are updated using locally available information and then the updates are sent to other storage locations.

In some embodiments, the geographic location of a device 405 may be determined by the GPS location of the device 405, such as through an internal or integrated GPS device. In these embodiments, the device 405 transmits the present GPS location to the service stack 415, which updates the database of devices 435. In other embodiments, the location of the device 405 may be determined based on the static IP address of the device 405, which is transmitted to the service stack 415. In still other embodiments, the location of the device 405 may be determined by interrogating the 3rd Generation Partnership Project (3GPP) location measurement unit (LMU). In these embodiments, the LMU may be interrogated by a specialized operation system that updates the database of devices 435. Furthermore, the location information may be carried in-band over the communications link between the device 405 and the service stack 415. The above embodiments are potential examples, and one having ordinary skill in the art would understand than there are many methods of determining the location of the device 405 that allow the systems to work as described herein.

In the exemplary embodiment, the optimizer 440 analyzes the data in the database of devices 435. Based on the analysis, the optimizer 440 may instruct the orchestrator 420 to move the service stack 415 associated with the device 405 to a different location on the network 410 or to a different network 410.

In some cases, this action may be triggered by an event, such as, but not limited to, computational overload at the present data center; reduction in the quality of services, which can be restored by relocating the service stack 415; a surge in the costs associated with the bandwidth; and a surge in the costs associated with the traversal of other networks. More specifically, this analysis may be triggered by a change in the database of devices 435. This is in situations where such changes are rare, such that the mean time t between database changes is less than the average analysis time T. Alternatively, the analysis may be conducted continuously, and thus be performed approximately every time period T.

In some embodiments, certain events may be considered higher priority events than others when determining whether to move the service stack 415. Examples of high priority events include, but are not limited to, if there is a significant reduction in available computational power or if the device enters a network that makes communications extremely expensive. If a high priority event occurs, then the optimizer 440 may restart the optimization process immediately.

In some cases, the determination of whether or not to move may be made by solving a set of linear (or integer) programming problems in which the cost function is minimized. As the device 415 moves, the desired result is that the path between the device 405 and the service stack 415 is the shortest path possible. In some embodiments, the metrics on each but the last link is determined by the cost of the bandwidth, with the constraint that the bandwidth is sufficient to maintain the required QoS. The last link (the link to the service stack 415) takes into account the computational power available in the data center hosting the service stack 415.

In the exemplary embodiment, the result of optimization includes both that the service stack 415 follows the device 405 and that the least-cost location is used for the device 405 even when the device 405 is stationary.

Figure 5:
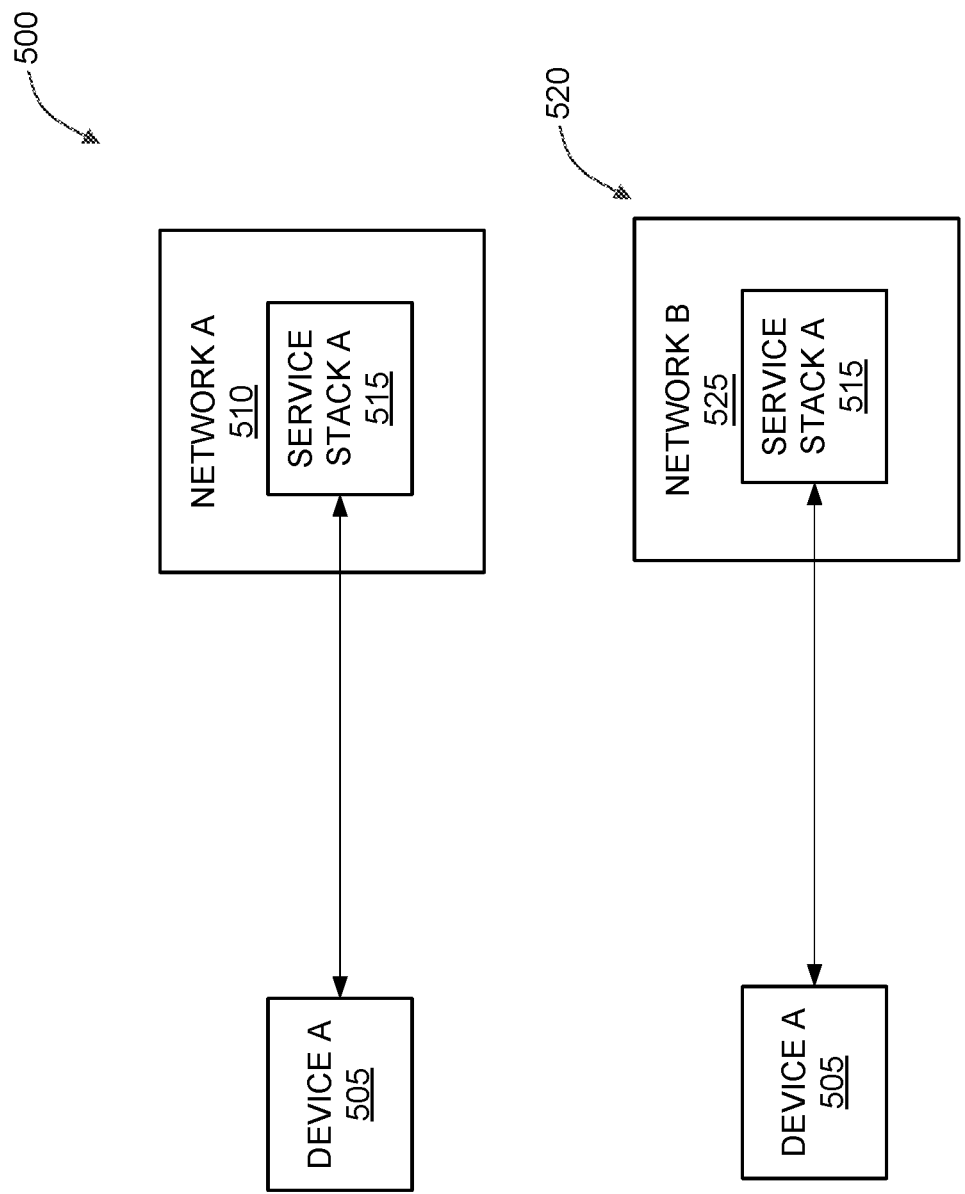
FIG. 5 is a schematic illustration of a roaming device connecting to multiple networks, according to an embodiment.

FIG. 5 is a schematic illustration of a roaming device 505 connecting to multiple networks 510 and 525, according to an embodiment. In at least one embodiment, device A 505 is connected to service stack A 515, where service stack A 515 is located on network A 510 at time A 500. In other embodiments, service stack A 515 could be location at data center A (not shown). At a later time B 520, service stack A 515 has moved to network B 525 or data center B (not shown).

Service stack A 515 may have moved when device A 505 changed location. Service stack A 515 may have also moved because of the cost of communication on network A 510 compared to the costs on network B 525.

In one example, at time A 500, the optimizer 440 (shown in FIG. 4) analyzes the connection between service stack A 515 and device A. The analysis may include information from the database of devices 435 (shown in FIG. 4). In this example, the optimizer 440 determines that it would be optimal to host the service stack A 515 on network B 525. The optimizer 440 instructs the orchestrator 420 (shown in FIG. 4) to move service stack A 515 to network B 525. The orchestrator 420 consults the policy engine 425 and the SLA engine 430 (both shown in FIG. 4) to determine whether it may transfer service stack A 515 to network B 525. Once the orchestrator 420 determines that the transfer is allowed, then the orchestrator 420 transfers service stack A 515 to network B 525 and updates the information for device A 505 in database of devices 435.

The computer-implemented methods discussed herein may include additional, less, or alternate actions, including those discussed elsewhere herein. The methods may be implemented via one or more local or remote processors, transceivers, and/or sensors (such as processors, transceivers, and/or sensors mounted on vehicles or mobile devices, or associated with smart infrastructure or remote servers), and/or via computer-executable instructions stored on non-transitory computer-readable media or medium.

Additionally, the computer systems discussed herein may include additional, less, or alternate functionality, including that discussed elsewhere herein. The computer systems discussed herein may include or be implemented via computer-executable instructions stored on non-transitory computer-readable media or medium.

A processor or a processing element may be trained using supervised or unsupervised machine learning, and the machine learning program may employ a neural network, which may be a convolutional neural network, a deep learning neural network, a reinforced or reinforcement learning module or program, or a combined learning module or program that learns in two or more fields or areas of interest. Machine learning may involve identifying and recognizing patterns in existing data in order to facilitate making predictions for subsequent data. Models may be created based upon example inputs in order to make valid and reliable predictions for novel inputs.

Additionally or alternatively, the machine learning programs may be trained by inputting sample (e.g., training) data sets or certain data into the programs, such as communication data of compromised and uncompromised devices, communication data from a wide variety of devices, and communication data of a wide variety of malicious sources. The machine learning programs may utilize deep learning algorithms that may be primarily focused on pattern recognition, and may be trained after processing multiple examples. The machine learning programs may include Bayesian program learning (BPL), voice recognition and synthesis, image or object recognition, optical character recognition, and/or natural language processing—either individually or in combination. The machine learning programs may also include natural language processing, semantic analysis, automatic reasoning, and/or other types of machine learning, such as deep learning, reinforced learning, or combined learning.

Supervised and unsupervised machine learning techniques may be used. In supervised machine learning, a processing element may be provided with example inputs and their associated outputs, and may seek to discover a general rule that maps inputs to outputs, so that when subsequent novel inputs are provided the processing element may, based upon the discovered rule, accurately predict the correct output. In unsupervised machine learning, the processing element may be required to find its own structure in unlabeled example inputs. The unsupervised machine learning techniques may include clustering techniques, cluster analysis, anomaly detection techniques, multivariate data analysis, probability techniques, unsupervised quantum learning techniques, associate mining or associate rule mining techniques, and/or the use of neural networks. In some embodiments, semi-supervised learning techniques may be employed. In one embodiment, machine learning techniques may be used to extract data about the device, network, policies, communications, activities, software, hardware, malicious code, and/or other data.

In the exemplary embodiment, a processing element may be trained by providing it with a large sample of communication data with known characteristics or features. Such information may include, for example, information associated with a specific device, type of device, device activity, network activity, software versions, and/or other data.

Based upon these analyses, the processing element may learn how to identify characteristics and patterns that may then be applied to analyzing communication data. For example, the processing element may learn, with the user's permission or affirmative consent, to identify the necessary upgrades necessary for attached device, potential security vulnerabilities associated with different software, and communication data associated with those security vulnerabilities being compromised. This information may be used to determine how to modify communications to and from the device to prevent compromise of other devices and networks.

The exemplary embodiments provided herein describe a network doppelganger, that is advantageously disposed within one or more of the operator network, the service provided, and the access network, to intercept the traffic emanating from the device/thing, and to communicate with other entities on behalf of the device/thing. The network doppelganger thus functions as a midbox capable of: (i) repeatedly evaluating the security properties of the device/thing and pro-actively taking measures to enforce the security thereof; (ii) protecting the network operator and service provider, as well as other system/network endpoints; and/or (iii) providing a point of enforcement for lawful interception. A security posture engine of the network doppelganger may therefore be configured, based on respective service provider and network operator policies imported and integrated in an integrated policy engine, to: (i) poll the device/thing for the validity and strength of the device password, and force changes where needed; (ii) check the integrity of the hardware and software of the device/thing (e.g., by attestation); (iii) force security software patches and other updates; and/or (iv) log essential device security events and reports the log to the service provider and/or the network operator.

The exemplary embodiments provided herein describe a service stack, that is advantageously disposed within one or more of network to monitor and managed the traffic emanating from the device/thing, and to communicate with other entities on behalf of the device/thing. The service stack thus functions as a midbox capable of: (i) rerouting the communications to and from the IoT device to ensure proper communications; (ii) improving the user experience (such as by shortening the delay and providing better jitter control); (iii) reduce the operator network's bandwidth by restricting the communications to the smallest network partition; (iv) reduce the central computational power by moving the computation to underutilized local hosts; and (v) follow the device geographically to ensure proper communications.

The improvements described herein may be achieved by performing one or more of the following steps: (a) execute an IoT device communication application, wherein the IoT device communication application monitors the IoT device; (b) store, in the at least one memory device, IoT device data including a current location of the IoT device; (c) determine an optimal communication path between the IoT device communication application and the IoT device based on the IoT device data; (d) transfer execution of the IoT device communication application to a second computing device based on the optimal communication path; (e) determine an updated location of the IoT device; (f) store, in the at least one memory device, the updated location; (g) determine the optimal communication path between the IoT device communication application and the IoT device based on the updated location; (h) determine a computational load of the first computing device; (i) update the IoT device data based on the determined computational load; (j) determine a computational load of the second computing device; (k) determine the optimal communication path based in part on the determined computational load associated with the first computing device and the computational load of the second computing device; (l) determine one or more statistics associated with a quality of service of the IoT device; (m) update the IoT device data based on the one or more statistics associated with the quality of service of the IoT device; (o) determine the optimal communication path based in part on the one or more statistics associated with the quality of service of the IoT device; (p) detect an update to the IoT data; and (q) determine the optimal communication path between the IoT device communication application and the IoT device based on the updated IoT device data.

The improvements described herein may also be achieved by performing one or more of the following steps: (a) analyze a plurality of computer devices to determine the optimal communication path; (b) for each of a plurality of locations for the IoT device communication application, determine a communication path between the IoT device and a location of the plurality of locations of the IoT device communication application, wherein each communication path includes a plurality of links; (c) compare the plurality of communication paths; (d) determine the optimal path based on the comparison; (e) calculate a metric for each of the plurality of links; (f) calculate the metric for the plurality of links based, at least in part, on the cost of the bandwidth; (g) calculate the metric for the plurality of links based, at least in part, on the cost of the bandwidth and the constraint that the bandwidth is sufficient to maintain the required quality of service; and (h) calculate the metric for the link connected to the IoT device communication application based, at least in part, on the computational power associated with the corresponding location of the plurality of locations hosting the IoT device communication application.

The aspects described herein may be implemented as part of one or more computer components such as a client device and/or one or more back-end components, such as a network doppelgänger, for example. Furthermore, the aspects described herein may be implemented as part of a computer network architecture and/or a cognitive computing architecture that facilitates communications between various other devices and/or components. Thus, the aspects described herein address and solve issues of a technical nature that are necessarily rooted in computer technology.

For instance, aspects include analyzing various sources of communication data to determine potential compromise of a connected device, monitor and update the security of the connected device, and facilitate communication with a roaming device. In doing so, the aspects overcome issues associated with having compromised devices infect other devices and ensuring proper communications between a device and a service provider. Furthermore, these aspects reduce the chance of data compromise and allow for proposer access to the communications. Without the improvements suggested herein, additional processing and memory usage, or even direct human intervention, would be required to perform such activities. Additional technical advantages include, but are not limited to: i) improved speed and responsiveness in communication with a connected device; ii) ensuring devices comply with policies of attached networks; iii) ensuring that devices are up to date with security practices and software updates; iv) reducing malicious communications; v) automatically intercepting and modifying malicious messages; and vi) allow for constant monitoring of the state of connected devices. Additional technical advantages are described in other sections of the specification.

Furthermore, the embodiments described herein improve upon existing technologies, and improve the functionality of computers, by more accurately predict or identify the current security status of any connected device. The present embodiments improve the speed, efficiency, and accuracy in which such calculations and processor analysis may be performed. Due to these improvements, the aspects address computer-related issues regarding efficiency over conventional techniques. Thus, the aspects also address computer related issues that are related to computer security, for example.

Accordingly, the innovative systems and methods described herein are of particular value within the realm of IoT devices, which have been historically associated with a poor record of securing communications and data. The present embodiments enable more reliable updating and control of such devices, but without compromising data and communications. Furthermore, according to the disclosed techniques, service providers and network operators are better able to monitor and update the security of connected IoT devices, and thereby protect other IoT devices on the network. Moreover, the ability to more reliably track devices, but without adding additional risk to consumer data, greatly enhances the ability of manufacturers to realize secondary market revenue for a device, such as in the case of software updates to the device programming, or new commercial opportunities that may be exploited in association with the device (e.g., marketing promotions, cross-sales, seasonal activities).

Exemplary embodiments of systems and methods for securing IoT devices are described above in detail. The systems and methods of this disclosure though, are not limited to only the specific embodiments described herein, but rather, the components and/or steps of their implementation may be utilized independently and separately from other components and/or steps described herein.

Although specific features of various embodiments may be shown in some drawings and not in others, this is for convenience only. In accordance with the principles of the systems and methods described herein, any feature of a drawing may be referenced or claimed in combination with any feature of any other drawing.

Some embodiments involve the use of one or more electronic or computing devices. Such devices typically include a processor, processing device, or controller, such as a general purpose central processing unit (CPU), a graphics processing unit (GPU), a microcontroller, a reduced instruction set computer (RISC) processor, an application specific integrated circuit (ASIC), a programmable logic circuit (PLC), a programmable logic unit (PLU), a field programmable gate array (FPGA), a digital signal processing (DSP) device, and/or any other circuit or processing device capable of executing the functions described herein. The methods described herein may be encoded as executable instructions embodied in a computer readable medium, including, without limitation, a storage device and/or a memory device. Such instructions, when executed by a processing device, cause the processing device to perform at least a portion of the methods described herein. The above examples are exemplary only, and thus are not intended to limit in any way the definition and/or meaning of the term processor and processing device.

This written description uses examples to disclose the embodiments, including the best mode, and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A midbox computing device for monitoring communications between a separate communication network and a separate connected Internet of Things (IoT) device, the midbox computing device comprising:
    at least one processor in communication with the IoT device; and
    at least one memory device configured to store a plurality of computer-executable instructions, which, when executed by the at least one processor, cause the at least one processor to:
        execute an IoT device communication application configured to monitor the IoT device;
        store, in the at least one memory device, IoT device data including a current geographic location of the IoT device;
        determine an optimal communication path between (i) a first network stack on which the IoT device communication application resides, and (ii) the IoT device, based on the stored geographic location IoT device data;
        calculate a first communication path between the IoT device and the first network stack disposed at a first network stack location for the IoT device communication application;
        calculate a second communication path between the IoT device and a second network stack disposed at a second network stack location, different from the first network stack location, for the IoT device communication application;
        compare the first and second communication paths;
        determine, based on the comparison of the first and second communication paths, that the second communication path is an optimal communication path; and
        transfer execution of the IoT device communication application from the first network stack to the second network stack based on the determined optimal communication path.

2. The system in accordance with claim 1, wherein the instructions further cause the at least one processor to:
    determine an updated geographic location of the IoT device; and
    store, in the at least one memory device, the updated geographic location.

3. The system in accordance with claim 2, wherein the instructions further cause the at least one processor to determine the optimal communication path between the first and second network stacks, respectively, and the IoT device based on the updated geographic location.

4. The system in accordance with claim 1, wherein the instructions further cause the at least one processor to:
    determine a computational load of the first computing device; and
    update the IoT device data based on the determined computational load.

5. The system in accordance with claim 4, wherein the instructions further cause the at least one processor to:
    determine a computational load of the second computing device; and
    determine the optimal communication path based in part on the determined computational load associated with the first computing device and the computational load of the second computing device.

6. The system in accordance with claim 1, wherein the instructions further cause the at least one processor to:
  determine one or more statistics associated with a quality of service of the IoT device; and
  update the IoT device data based on the one or more statistics associated with the quality of service of the IoT device.

7. The system in accordance with claim 6, wherein the instructions further cause the at least one processor to determine the optimal communication path based in part on the one or more statistics associated with the quality of service of the IoT device.

8. The system in accordance with claim 1, wherein the IoT device communication application facilitates communication between the IoT device and one or more additional networks different from the communication network.

9. The system in accordance with claim 1, wherein the instructions further cause the at least one processor to
  detect an update to the IoT device data; and
  determine the optimal communication path between the first and second network stacks, respectively, and the IoT device based on the updated IoT device data.

10. The system in accordance with claim 1, further comprising an optimizer, wherein the optimizer is configured to determine the optimal communication path between the first and second network stacks, respectively, and the IoT device.

11. The system in accordance with claim 1, wherein the instructions further cause the at least one processor to analyze a plurality of computer devices to determine the optimal communication path.

12. The system in accordance with claim 1, wherein each of the first and second communication paths includes a plurality of links, and wherein the instructions further cause the at least one processor to calculate a metric for each of the plurality of links.

13. The system in accordance with claim 12, wherein the instructions further cause the at least one processor to calculate the metric for the plurality of links based, at least in part, on a bandwidth cost.

14. The system in accordance with claim 13, wherein the instructions further cause the at least one processor to calculate the metric for the plurality of links based, at least in part, on the bandwidth cost of the bandwidth and a constraint that bandwidth is sufficient to maintain a required quality of service.

15. The system in accordance with claim 13, wherein the instructions further cause the at least one processor to calculate the metric for the link connected to the IoT device communication application based, at least in part, on a computational power associated with the corresponding location of the plurality of locations hosting the IoT device communication application.

16. A method for monitoring communications between a communication network and a connected Internet of Things (IoT) device, the method being implemented midbox computing device different from the communication network and the IoT device, the midbox computing device including a least one processor and at least one memory device, the method comprising steps of:
  executing an IoT device communication application configured to monitor the IoT device;
  storing, in the at least one memory device, IoT device data including a current geographic location of the IoT device;
  determining an optimal communication path between (i) a network stack on which the IoT device communication application resides, and (ii) the IoT device, based on the stored geographic location IoT device data; and
  calculating a first communication path between the IoT device and the first network stack disposed at a first network stack location for the IoT device communication application;
  calculating a second communication path between the IoT device and a second network stack disposed at a second network stack location, different from the first network stack location, for the IoT device communication application;
  comparing the first and second communication paths;
  determining, based on the comparison of the first and second communication paths, that the second communication path is an optimal communication path; and
  transfering execution of the IoT device communication application from the first network stack to the second network stack based on the determined optimal communication path.

17. The method in accordance with claim 16, further comprising steps of:
  determining an updated geographic location of the IoT device;
  storing, in the at least one memory device, the updated geographic location; and
  determine the optimal communication path between the first and second network stacks, respectively, and the IoT device based on the updated geographic location.

18. The method in accordance with claim 16, further comprising steps of:
  determining a computational load of the first computing device;
  updating the IoT device data based on the determined computational load;
  determining a computational load of the second computing device; and
  determining the optimal communication path based in part on the determined computational load associated with the first computing device and the computational load of the second computing device.

* * * * *